United States Patent
Pitzer et al.

(10) Patent No.: US 6,531,487 B2
(45) Date of Patent: Mar. 11, 2003

(54) INDOLO[2,1-B] QUINAZOLE-6, 12-DIONE ANTIMALARIAL COMPOUNDS AND METHODS OF TREATING MALARIA THEREWITH

(75) Inventors: Kevin K. Pitzer, Pasadena, MD (US); John P. Scovill, Walkersville, MD (US); Dennis E. Kyle, Gaithersburg, MD (US); Lucia Gerena, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 13 days.

(21) Appl. No.: 09/850,996

(22) Filed: May 8, 2001

(65) Prior Publication Data

US 2001/0034350 A1 Oct. 25, 2001

Related U.S. Application Data

(62) Division of application No. 09/407,196, filed on Sep. 28, 1999, now Pat. No. 6,284,772.
(60) Provisional application No. 60/102,399, filed on Sep. 30, 1998.

(51) Int. Cl.$^7$ .......................... A61K 31/47; A61K 31/65
(52) U.S. Cl. .................. 514/308; 514/152; 514/895
(58) Field of Search .................... 514/308, 152, 514/895

(56) References Cited

U.S. PATENT DOCUMENTS 5,441,955 A * 8/1995 Baker et al. ................. 514/250
6,284,772 B1 * 9/2001 Pitzer et al. ................. 514/308

FOREIGN PATENT DOCUMENTS

| EP | 0708375 A | | 4/1996 |
| EP | 0718298 A | | 6/1996 |
| JP | 09095621 | | 4/1997 |
| WO | WO95 13807 | | 5/1995 |
| WO | 00/18769 | * | 4/2000 |

OTHER PUBLICATIONS

Windholz et al., The Merck Index, Tenth Edition (1983) p. 499, abstract No. 3436.*
Lin, Ai J. et al., Antimalarial Activity of New Dihydroartemisinin Derivatives. 7.4-(p–Suibstituted phenyl)-4(R or S)-[10(a or b)-dihydroartemisininoxy] butyric Acids 1-6, J. Med. Chem. 1997, 40, 1396–1400.
Bermudez, et al., Mefloquine is Active In Vitro and In Vivo against Mycobacterium avium Complex, Antimicrobial Agents and Chemotherapy, Aug. 1999, p. 1870–1874.
Schrenk, et al., Tryptanthrins: A Novel Class of Agonists of the Aryl Hydrocarbon Receptor, Biochemical Pharmacology, vol. 54, 1997, pp. 165–171.
Fiedler, et al., toffwechselprodukte von Mikroorganismen, Microbiol., 107, 1976, p249–256.
Kikumoto, et al., The Reactions of Oxindoles and Isatin with Nitrobenzyl Chlorides, Tetrahedron, vol. 22, 1966, pp3337–3343.
Eguchi, et al., Short–Step Synthesis of Rutecarpine and Tryptanthrin Via Intramolecular AZA–Wittig Reaction1, Heterocycles, vol. 33, No. I, 1992, p153–156.
Staskun, New approach to the indolo[2,1–b]quinazoline ring system by cyclization of 3-(o-cgkiriogebtk)-2-methyl-4(3H)-quinazollinone and its m–isomer. Systhesis of the antibiotic tryptanthrin, S. Afr. J. Chem, 45(1), 1992, pp. 5–7.
Mitscher, et al., Tuberculosis: A Search for Novel Therapy Starting with Natural Products, Medicinal Research Reviews, 18(6), Nov. 1998.
Friedlander, c.R.–P. 276808, vom 12. Juni 1913 (ausgegben 15. Juli 1914), pp1843–1844.
Karpf, et al. Thermolyse Von Isatin Mittels Eines, Tetrahedron Letters, No. 33, pp3007–3008, 1978.

(List continued on next page.)

Primary Examiner—Kevin E. Weddington
(74) Attorney, Agent, or Firm—Elizabeth Arwine

(57) ABSTRACT

Compounds, compositions and methods are provided for treating malaria parasites in vitro and in vivo by administering indolo[2,1-b]quinazoline-6,12-dione compounds of Formula I.

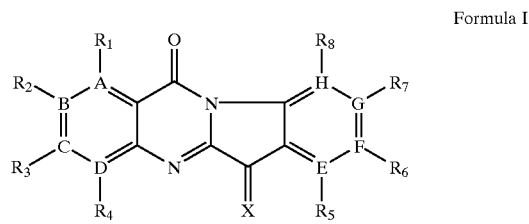

Formula I wherein A, B, C, D, E, F, G and H are independently selected from carbon and nitrogen, or A and B or C and D can be taken together to be nitrogen or sulfur, with the proviso that not more than three of A, B, C, D, E, F, G and H are other than carbon; wherein $R_1$ through $R_8$ are independently selected from the group consisting of, but not limited to, the halogens (F, Cl, Br, and I), alkyl groups, trifluoromethyl groups, methoxyl groups, the carboxy methyl or carboxy ethyl group ($COOCH_3$ or $COOCH_2CH_3$), nitro, aryl, heteroaryl, cyano, amino, dialkylaminoalkyl, 1-(4-alkylpiperazinyl), and the pharmaceutically acceptable salts thereof; and wherein X is independently selected from the group consisting of any atom especially oxygen, or any side chain necessary to make the indolo[2,1-b]quinazoline-6,12-dione compound a "prodrug" as the term is understood by one of ordinary skill in the art of medicinal chemistry. In other words, a side chain having a structure where a carbon-nitrogen double bond bears substituents that make the prodrug more water soluble and bioavailable.

18 Claims, No Drawings

OTHER PUBLICATIONS

Mitscher, Antimicrobial Agents From Higher Plants. New Synthesis and Bioactivity of Tryptanthrin (indolo–[2,1–b] quinazolin–6,12–dionne) and its analogues, Heterocycles, vo.l. 15, No. 2, 1981, pp1017–1021.

Brufani, et al. Specialia, Experientia, vol. 27–Fasc.11, Nov. 15, 1971, pp. 1249–1376.

Bergman, et al., The Structure of Some Indolic Constituents In Couroupita Guaianensis Aubl., Tetrahedron LettersNo. 30, 1977, pp2625–2626.

Gassman, et al., A General Method for the Systhesis of Isatins, J.Org.Chem., vol., 42, No. 8, 1977, pp1344–1348.

Capuano, et al., Neue Synthese und Cycloreaktionen der a–Acyl–und a–Sulfonyl–ketenimine, Chem. Ber. 116, 741–750 (1983).

Mitschler, L.A. et al., A Search for Novel Chemotherapy Against Tuberculosis Amongst Natural Products, Pure & Appl.Chem, vol. 70, No. 2, 1998, pp. 365–371, XP000872938, London.

Mitscher, et al., Antimicrobial Agents Form Higher Plants, New Synthesis and Bioactivity of Traptanthrin (indolo–'2, 1–b?quinazolin–6,12–dione) and its analogues, Heterocycles, vol. 15, No. 2, 1981, pp. 1017–1021, XP000872254, sendal.

Grandoline, et al., Synthesis and Antimicrobial Activity of Some New Derivatives of 6,12–Dihydroindolo '2,1–b?quinazolin–6,12–dione, IL FARMACO, vol. 52, No.11, 1997, pp. 679–683, XP000872649, ROM.

Bringmann, et al., First Synthesis of the Antimalarial Naphthytlisoquinoline Alkaloid Dioncophylline C. and its unnatural Anti–HIV Dimer, Jozimine C, Tetrahedron, NL, Elsevier Science Publishers, Amsterdam, vo. 54, No. 3–4, Jan. 15, 1998, XP004106638.

Iwasa, et al., Antimalarial Activity and Structure–Activity Relationships of Protoberberine Alkaloids, European Journal of Medicinal Chemestry.Chimica Therapeutica, FR, Editions Scientifique Elsevier, Paris, vol. 33, No. 1, Jan. 1998, pp. 65–69, XP004173057.

Puri, et al., Antibiotics in the Chemotherapy of Malaria, Progr.Drug Res, vol. 19, 1982, pp. 269–331, XP000881096, Basel. Boston. Berlin.

* cited by examiner

INDOLO[2,1-B] QUINAZOLE-6, 12-DIONE ANTIMALARIAL COMPOUNDS AND METHODS OF TREATING MALARIA THEREWITH

This application is a divisional application of Ser. No. 09/407,196, filed Sep. 28, 1999 now 6,284,772, claiming benefit of priority of provisional application No. 60/102,399 filed Sep. 30, 1998.

FIELD OF THE INVENTION

The present invention relates to new and existing indolo [2,1-b]quinazoline-6,12-dione derivatives which are useful in killing malaria parasites, antimalarial compositions containing the compounds, and to methods of treating malaria with the compounds and compositions, alone or in combination with other antimalarial agents both in vitro and in vivo.

BACKGROUND OF THE INVENTION

The current global situation in respect to malaria has recently been detailed by Peters [W. Peters, "Drug Resistance in Malaria Parasites of Animals and Man", Advances in Parasitology, vol. 41, pp 1–62 (1998)]. Currently, about two billion people are exposed to malaria and 400 million are infected with the disease. Between 100–200 million new cases occur each year. There are approximately 1–2 million deaths annually due to malaria. The global situation is worsening. The pertinent facts are these: very few new antimalarial drugs have been introduced in the past quarter century; there is massive pressure for the development of drug resistance due to the presence of large numbers of non-immune people in areas where malaria is efficiently transmitted; and resistance by *Plasmodium falciparum* and *Plasmodium vivax* to chloroquine is being documented in an increasingly wide geographic area.

Other frontline drugs currently used for the treatment and prevention of malaria such as mefloquine and halofantrine, are becoming increasingly ineffective. Newly introduced artemsinin analogs (artesunate and artemether), while effective for the treatment of malaria, may be too toxic for long term administration required for prophylaxis. As a result, the idea of malaria eradication has been abandoned and replaced with the more realistic target of malaria control.

Indolo[2,1-b]quinazoline-6,12-dione is a compound with a long history [see C. W. Bird, Tetrahedron, 19, 901 (1963), and references therein]. The structure of the compound has been verified by x-ray crystallography: M. Brufani, et al., Experientia, 27, 1249 (1971); W. Fedeli, et al., J. Chem. Soc. Perkin Transactions 2, 621 (1974). Early developments were described by Friedlander and Reschdestwensky [Ber., 48, 1843 (1915). Numerous synthetic approaches to the parent compound have been described: H. Karpf, et al., Tet. Let, 3007 (1978); L. A. Mitscher, et al., Heterocycles, 15, 1017 (1981); L. Capuano, et al., Chem. Ber., 116, 741 (1983); S. Euguchi, et al., 33, 153 (1992). Indolo[2,1-b]quinazolo-6, 12-dione is also a naturally occurring compound, that is found in the higher plants such as *Couroupita guianensis* Aubl [Bergman, et al., Tet. Let., 2625 (1977)]; *Strobilanthes cusia* [G. Honda, et al., Planta Medica, 37, 172, (1979)]; *Polygonum tinctorum* and *Isatis tinctorum* [G. Honda, et al., Planta Medica, 38, 275 (1980). It is produced by *Candida liplytica* when grown in media containing an excess of tryptophan, hence its name, tryptanthrin. Indolo[2,1-b] quinzoline-6,12-dione has been shown to possess antibacterial activity against a variety of pathogenic bacteria, particularly the causative agent of tuberculosis, Mycobacterium tuberculosis. Antibacterial activity is also claimed against *Staphylococcus aureus, Klebsiella pneumoniae, Mycobacterium smegmatis*, and the fungi, *Candida albicans* [Mitscher, et al., "Antimicrobial Agents from Higher Plants. New Synthesis and Bioactivity of Tryptanthrin (Indolo[2,1-b]quinazoline-6,12-dione) and its Analogues", Heterocycles 15, 1017–1021 (1981); Honda, G. and Tabata., M., "Isolation of Antifungal Principal Tryptanthrin from *Strobilanthes Cusia* O. Kuntze,", Planta Medica, J Med. Plant Res., 36, 85–86 (1979); Mitscher, et al., "Part I. Antitubercular Agents from Higher Plants: Synthesis and In Vitro Activity of Indolo[2,1-b]quinazoline-6,12-diones and Related Analogs", Abstracts of Papers, 35 International Congress of Antimicrobial Agents and Chemotherapy, Abstract F 16, San Diego, Calif., 1995; Baker, W. "Part II. Antitubercular Agents from Higher Plants: Antimycobacterial Activity of Azaindoloquinazolines. Novel Agents against Sensitive and Multi-drug Resistant Tuberculosis", Abstracts of Papers, 35 International Congress of Antimicrobial Agents and Chemotherapy, Abstract F17, San Diego, Calif., 1995. To date, however, there has been no evidence or indication that Indolo[2,1-b]quinazoline-6,12-dione and derivatives exhibit anti-malarial activity against malaria parasites or would be useful in treating malaria in vivo or in vitro.

Historically, the first antimalarial drugs stemmed from natural remedies. The quinchona alkaloids were utilized for centuries before their active principals, alkaloids such as quinine and quinidine, were isolated and shown to be effective in themselves against malaria. These compounds are devoid of useful clinical antibacterial activity. The discovery of the first synthetic antimalarial drugs was prompted by the selective staining of plasmodium tissues by vital stains. This lead, based upon the organic chemistry of synthetic dyes, led after a period of perhaps twenty years, to the discovery of two classes of quinoline antimalarial drugs, the 4-aminoquinolines (such as chloroquine) and the 8-aminoquinolines (such as primaquine). The biochemical basis of the antimalarial action of these agents, despite investigations spanning the last 50 years, is still unknown. Notwithstanding their extensive use as antimalarial agents, these compounds have found no clinical utility against bacterial species.

Some antibacterial agents have found application in the therapy and prevention of malaria. These include compounds whose mechanisms of antibacterial action are well documented. Those interfering with folate metabolism are the best known. These include the drug combination pyrimethamine-sulfadoxine, and dapsone. However, well known antimalarials which inhibit the metabolism of folate within the plasmodium, such as proguanil and cycloguanil, have not found application as antibacterial agents despite their extensive clinical application as antimalarial drugs. Doxycycline is used for malaria prophylaxis, and recently azithromycin C has shown antimalarial activity. Many extremely powerful antibacterial agents, such as the penicillins and cephalosporins, are devoid of antimalarial activity.

U.S. Pat. No. 5,441,955, the disclosure of which is expressly incorporated herein by reference, describes the general Formula I described herein, with the exception that it does not disclose that X can be a side chain necessary to make the compound of Formula I a prodrug. However, the '955 patent focuses on antibacterial compounds for treating bacterial infections, but fails to contemplate treating malaria parasites with these compounds or using them as antimalarial agents. Thus, the inventors of this invention have discovered the unexpected result of these particular compounds, and the compounds with side chains rendering the compounds prodrugs, as antimalarial agents.

That there is little relationship between antibacterial activity in a drug such as described in the '955 patent and antimalarial activity in a drug is not surprising. The bacteria and the plasmodia are very distant genetically: Bacteria are prokaryotes and plasmodia are eukaryotes. Thus, the search for acceptable antimalarial drugs is more difficult than the search for antibacterials as the metabolic processes of the plasmodia more closely resemble those of their eukaryotic hosts while the genetic and metabolic gap between bacterial and mammals is large as they belong to different kingdoms. Hence, an agent that is useful for treating a bacterial infection is not necessarily useful for treating a parasitic infection like malaria.

SUMMARY OF THE INVENTION

The inventors of the present invention have surprisingly discovered that Indolo[2,1-b]quinazoline-6,12-dione, and substituted derivatives, exhibit potent in vitro antimalarial activity against *Plasmodium falciparum*. Highly active compounds show $IC_{50}$ values (50% inhibitory concentration) in the 0.43 to 10 ng/mL concentration range, about one one-thousandth of the concentrations necessary to inhibit bacteria. Furthermore, these compounds are also highly active against strains of *Plasmodium falciparum* which are up to 5000-fold resistant to atovoquone, 50-fold resistant to chloroquine, and 20-fold resistant to mefloquine. Therefore, this invention provides methods for inhibiting the growth of malaria parasites in vitro and provides methods for the prevention and treatment of malaria in vivo using indolo[2,1-b]quinazoline-6,12-dione compounds of formula I.

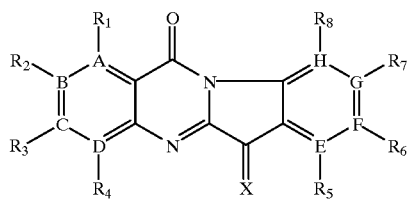

Formula I wherein A, B, C, D, E, F, G and H are independently selected from carbon and nitrogen, or A and B or C and D can be taken together to be nitrogen or sulfur, with the proviso that not more than three of A, B, C, D, E, F, G and H are other than carbon; wherein $R_1$ through $R_8$ are independently selected from the group consisting of, but not limited to, the halogens (F, Cl, Br, and I), alkyl groups, trifluoromethyl groups, methoxyl groups, the carboxy methyl or carboxy ethyl group ($COOCH_3$ or $COOCH_2CH_3$), nitro, aryl, heteroaryl, cyano, amino, dialkylaminoalkyl, 1-(4-alkylpiperazinyl), and the pharmaceutically acceptable salts thereof; and wherein X is independently selected from the group consisting of any atom especially oxygen, or any side chain necessary to make the indolo[2,1-b]quinazoline-6,12-dione compound a "prodrug" as the term is understood by one of ordinary skill in the art of medicinal chemistry. In other words, a side chain having a structure where a carbon-nitrogen double bond bears substituents that make the prodrug more water soluble and bioavailable. Improved bioavailability results in a lower effective dosage. It also makes more predictable and uniform absorbance which increases the predictability of the response which in turn increases safety by reducing drug side effects.

An example of a prodrug containing a labile carbon-nitrogen double bond side chain exocyclic to the tryptanthin structure is shown in Formula II. Such an example may be more water soluble, but can be readily converted to the tryptanthrin structure through hydrolysis of the carbon-nitrogen bond to give tryptanthrin.

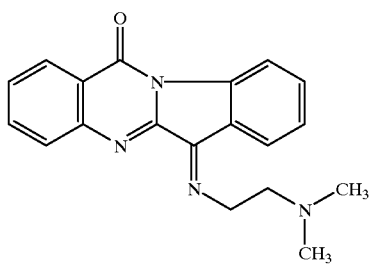

Formula II

Another example of a labile structure attached to the keto position which can increase the aqueous solubility of the tryptanthrin nucleous, but will be hydrolysed back to tryptanthrin in the blood stream is shown in Formula III.

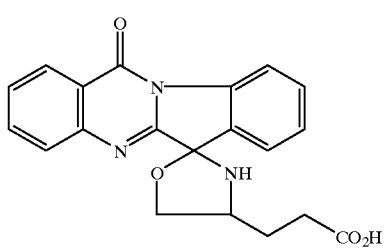

Formula III

These examples of prodrugs are not intended to limit the invention in any way. Other side chains are contemplated that would make the indolo[2,1-b]quinazoline-6,12-dione compound of the above formula I a prodrug as the term is understood by one of ordinary skill in the art of medicinal chemistry. Prodrugs are described in Medicimal Chemestry Principles and Practice, Frank D. Cane, Royal Society of Chemistry, Cambridge England, Chapter 14, pp215–218 (1994), which is herein incorporated by reference.

DETAILED DESCRIPTION OF THE PREFERRED EMBODIMENT

In accordance with the present invention, an antimalarial compound, composition and methods are provided for treating or control of strains of *Plasmodium falciparum, Plasmodium ovale, Plasmodium malariae* and *Plasmodium vivax*, either in vitro or in vivo by administering the compound or composition of the present invention. Thus, one aspect the present invention provides a method of inhibiting the growth of strains of *P. falciparum, Plasmodium ovale, Plasmodium malariae* and *P. vivax* in vitro comprising contacting the strains of *P. falciparum, Plasmodium ovale, Plasmodium malariae* and *P. vivax* with a growth inhibitory amount of a indolo[2,1-b]quinazoline-6,12-dione compound of the formula I.

In a second aspect, the invention provides methods for inhibiting the growth of malaria parasites in vitro and provides methods for the prevention and treatment of malaria in vivo using indolo[2,1-b]quinazoline-6,12-dione compounds of formula I.

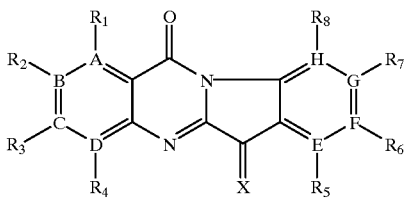

Formula I wherein A, B, C, D, E, F, G and H are independently selected from carbon and nitrogen, or A and B or C and D can be taken together to be nitrogen or sulfur, with the proviso that not more than three of A, B, C, D, E, F, G and H are other than carbon; wherein $R_1$ through $R_8$ are independently selected from the group consisting of the halogens (F, Cl, Br, and I), alkyl groups, trifluoromethyl groups, methoxyl groups, the carboxy methyl or carboxy ethyl group ($COOCH_3$ or $COOCH_2CH_3$), nitro, aryl, heteroaryl, cyano, amino, dialkylaminoalkyl, 1-(4-alkylpiperazinyl), and the pharmaceutically acceptable salts thereof; further wherein X is independently selected from the group consisting of any atom especially oxygen, or any side chain necessary to make the indolo[2,1-b]quinazoline-6,12-dione compound a "prodrug" as described above and as the term is understood by one of ordinary skill in the art of medicinal chemistry.

In another aspect, the present invention proposes methods of treating human or animal subjects suffering from a malarial infection, e.g., whether of sensitive-strain or multi-drug resistant strain (MDR-malaria) origin. Thus, the present invention provides a method of treating a human or animal subject in need of such treatment comprising administering to the subject a therapeutically effective amount of a indolo[2,1-b]quinazoline-6,12-dione compound of formula (I), above, either alone or in combination with other antimalarial agents or adjuvants.

Other antimalarial agents that can be used in combination with the compounds of the present invention include mefloquine, halofantrine, artesunate, artemether, chloroquine halofantrine, primaquine, sulfadoxine, sulfalene, pyrimethamine, doxycycline, tetracycline, azithromycin, proguanil, cycloguanil, dapsone, artemsinin, atovoquone and the like to name a few. These compounds can be combined with the compounds of the present invention in the same dosage, in a tablet, injectable liquid, or any other known form of administering drugs. These compounds can also be administered to a patient in a separate dosage.

Other adjuvants that can be used in combination with the compounds of the present invention are any other antiparasitic drugs.

The term "acylamino" means an acyl (CO—) radical to which an amino group is appended.

The term "loweralkyl" as used herein refers to branched or straight chain alkyl groups comprising one to ten carbon atoms, including, e.g., methyl, ethyl, propyl, isopropyl, n-butyl, t-butyl, neopentyl and the like.

The term "alkoxy" as used herein refers to RO wherein R is loweralkyl as defined above. Representative examples of lower alkoxy groups include methoxy, ethoxy, t-butoxy and the like.

The term "alkenyl" as used herein refers to a branched or straight chain groups comprising two to twenty carbon atoms which also comprises one or more carbon—carbon double bonds. Representative alkenyl groups include 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "alkynyl" as used herein refers to a branched or straight chain comprising two to twenty carbon atoms which also comprises one or more carbon—carbon triple bonds. Representative alkynyl groups include ethynyl, 2-propynyl (propargyl), 1-propynyl and the like.

The term "aryl" as used herein refers to a phenyl or a C9- or C10-bicyclic carbocyclic ring system having one or more aromatic rings, including naphthyl, tetrahydronaphthyl indanyi, indenyl and the like. Aryl groups can be unsubstituted or substituted with one, two or three substituents independently selected from loweralkyl, haloalkyl, alkoxy and halo.

The term "arylalkyl" as used herein refers to a lower alkyl radical to which is appended an aryl group. Representative arylalkyl groups include benzyl, phenylethyl, hydroxybenzyl, fluorobenzyl, fluorophenylethyl and the like.

The term "arylalkylaryl" as used herein refers to an arylalkyl group as previously defined appended to an aryl group. Representative arylalkylaryl groups include 4-benzylphenyl, 3-benzylphenyl, 4-phenethylphenyl and the like.

The term "arylaryl" as used herein refers to an aryl group as previously defined which is appended to an aryl group. Representative arylaryl groups include biphenyl, 4-(1-naphthyl)phenyl, 4-(2-naphthyl)phenyl and the like.

The term "aryloxy" as used herein refers to RO wherein R is an aryl group. Representative arylalkoxy groups include benzyloxy, phenylethoxy and the like.

The term "arylalkoxy" as used herein refers to a lower alkoxy radical to which is appended an aryl group. Representative arylalkoxy group include benzyloxy, phenylethoxy and the like.

The term "aryloxyaryl" as used herein refers to an aryl radical to which is appended an aryloxy group. Representative aryloxyaryl groups include 4-phenoxybenyl, 3-phenoxyphenyl, 4-phenoxy-1-naphthyl, 3-phenoxy-1-naphthyl and the like.

The term "aryloxyarylalkyl" as used herein refers to an arylalkyl radical to which is appended an aryloxy group. Representative aryloxyarylalkyl groups include 4-phenoxyphenylmethyl, 3-phenoxyphenylmethyl, 4-phenoxyphenylethyl, 3-phenoxyphenylethyl and the like.

The term "arylalkoxyaryl" as used herein refers to an aryl radical to which is appended an arylalkoxy group. Representative arylalkoxyaryl groups include 4-benzyloxyphenyl, 3-benzyloxyphenyl and the like.

The term "arylalkoxyarylalkyl" as used herein refers to an arylalkyl radical to which is appended an arylalkoxy group. Representative arylalkoxyarylalkyl groups include 4-benzyloxybenzyl, 3-benzyloxybenzyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "halogen" or "halo" as used herein refers to iodo, bromo, chloro or fluoro and the like.

The term "haloalkyl" as used herein refers to a lower alkyl radical, as defined above, bearing at least one halogen substituent, for example, chloromethyl, fluoroethyl or trifluoromethyl and the like.

The term "heterocycle" as used herein refers to an aromatic ring system composed of 5 or 6 atoms selected from the heteroatoms nitrogen, oxygen, and sulfur. The heterocycle may be composed of one or more heteroatoms that are either directly connected such as pyrazole or connected through carbon such as pyrimidine. Heterocycles can be substituted or unsubstituted with one, two or three substituents independently selected from amino, alkylamino, halogen, alkyl acylamino, lower alkylaryl, alkoxy.

The term "substituted heterocycle" or "heterocyclic group" or heterocycle as used herein refers to any 3- or 2,5 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0–2 double bonds and the 6-membered ring has 0–3 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. Heterocyclics in which nitrogen is the heteroatom are preferred. Fully saturated heterocyclics are also preferred.

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers or single enantiomers of the compounds of the invention are included in the present invention. Examples thereof are shown in Table 1, Example No. 34, 35, 71, 73 and 85. The terms "S" and "R" configuration, as used herein, are as defined by the IUPAC 1974 *Recommendations for Section E, Fundamental Stereochemistry, Pure Appl Chem.* (1976) 45, 13–30. The terms α and β are employed for ring positions of cyclic compounds. The α-side of the reference plane is that side on which the preferred substituent lies at the lowered numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by *the Chemical Abstracts Index Guide-Appendix IV* (1987) paragraph 203.

In yet a further aspect of the present invention, pharmaceutical compositions are provided which comprise a compound of the present invention in combination with a pharmaceutically acceptable carrier.

EXAMPLE 1

In vitro Inhibition of *Plasmodium falciparum*

The in vitro assays were conducted by using a modification of the semiautomated microdilution technique of Desjardins et al.[11] and Chulay et al.[12] Two strains of *Plasmodium falciparum* clones, from CDC Indochina III (W-2), CDC Sierra Leone I (D-6). The W-2 clone is susceptible to mefloquine but resistant to chloroquine, sulfadoxine, pyrimethamine, and quinine. The D-6 clone is resistant to mefloquine but susceptible to chloroquine, sulfadoxine, pyrimethamine, and quinine. They were derived by direct visualization and micromanipulation from patient isolates.[13] Test compounds were initially dissolved in DMSO and diluted 400-fold in RPMI 1640 culture medium supplemented with 25 mM Hepes, 32 mM $HaHCO_3$, and 10% Albumax I® (GIBCO BRL, Grand Island, N.Y.). These solutions were subsequently serially diluted 2-fold with a Biomek 1000® (Beckman, Fullerton, Calif.) over 11 different concentrations. The parasites were exposed to serial dilutions of each compound for 48 h and incubated at 37° C. with 5% $O_2$, 5% $CO_2$, and 90% $N_2$ prior to the addition of [$^3$H]hypoxanthine. After a further incubation of 18 h, parasite DNA was harvested from each microtiter well using Packard Filtermate 196 Harvester® (Meriden, Conn.) onto glass filters. Uptake of [$^3$H]hypoxanthine was measured with a Packard Topcount scintillation counter. Concentration-response data were analyzed by a nonlinear regression logistic dose-response model, and the IC50 values (50% inhibitory concentrations) for each compound were calculated (see Table 1, values within parentheses ( )). This procedure was repeated with the test compounds initially dissolved in DMSO and diluted 400-fold in RPMI 1640 culture medium supplemented with 25 mM Hepes, 32 mM $HaHCO_3$, and with blood serum replacing the 10% Albumax I® (see Table 1, figures without parentheses). The values without parentheses indicate culture in blood serum which more closely resemble conditions in a living animal.

Four strains of *Plasmodium falciparum* clones, from CDC Indochina III (W-2), CDC Sierra Leone I (D-6), Thai WR75-TM9, and Thai TM90C2B were utilized in susceptibility testing and the $IC_{50}$ results appear in Table 1.

TABLE 1

In Vitro Antimalarial Activity. Concentration of Indolo[2,3-b]quinazoline-6,12-dione
Inhibiting uptake of [$^3$H]Hypoxanthine by Parasitized Red Blood Cells by 50% ($IC_{50}$, ng/mL)

| Example No. | Structure | $IC_{50}$ (W-2) | $IC_{50}$ (D-6) | $IC_{50}$ (TM90C2B) | $IC_{50}$ (WR75-TM9) |
|---|---|---|---|---|---|
| 1. | 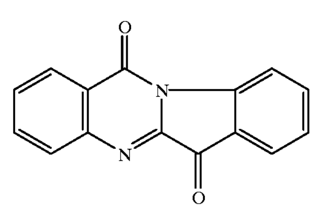 | (69)* | (69) | | |

TABLE 1-continued
In Vitro Antimalarial Activity. Concentration of Indolo[2,3-b]quinazoline-6,12-dione
Inhibiting uptake of [³H]Hypoxanthine by Parasitized Red Blood Cells by 50% (IC$_{50}$, ng/mL)
| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 2. | 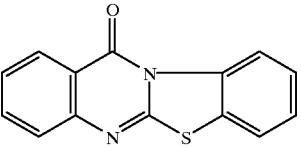 | (15626) | (12481) | | |
| 3. | 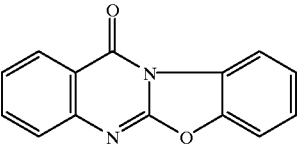 | (>50000) | (>50000) | | |
| 4. | 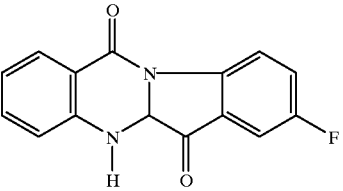 | (2.33) 15.335* | (4.07) 18.888 | 29.846 | 27.319 7.165 |
| 5. | 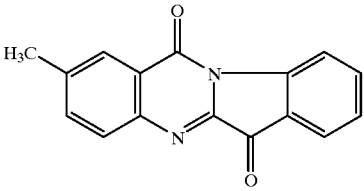 | (263.86) | (313.106) | | |
| 6. | 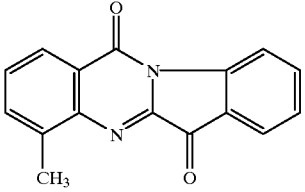 | (502.79) | (527) | | |
| 7. | 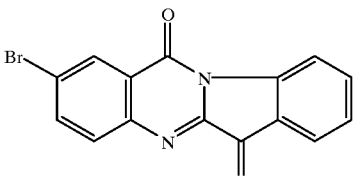 | (512.7) | (576.53) | | |
| 8. | 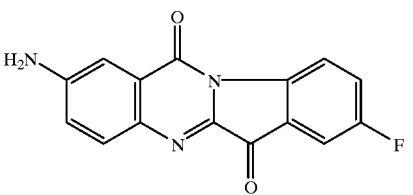 | (62) | (62) | | |

TABLE 1-continued

In Vitro Antimalarial Activity. Concentration of Indolo[2,3-b]quinazoline-6,12-dione
Inhibiting uptake of [³H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 9. | 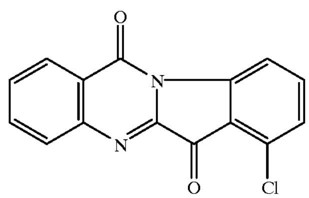 | (403) | (471) | | |
| 10. | 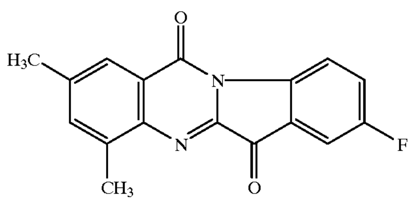 | (131) | (138) | | |
| 11. | 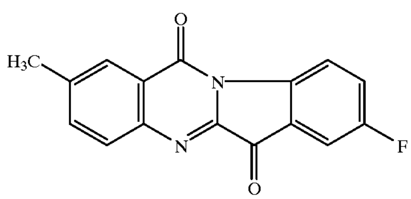 | (2.8) 14.678 | (4.9) 22.068 | 16.383 | 35.991 1.587 |
| 12. | 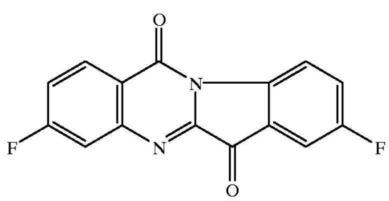 | (1.6) 5.274 5.787 6.539 | (4.9) 8.535 14.239 11.005 | 9.738 16.914 11.113 | 11.951 16.249 19.374 |
| 13. | | (5.1) 4.335 | (14.3) 14.842 | 10.531 | 9.837 21.542 |
| 13. | | (5.8) 10.091 | (10.0) 23.258 | 20.119 | 10.499 |
| 14. | 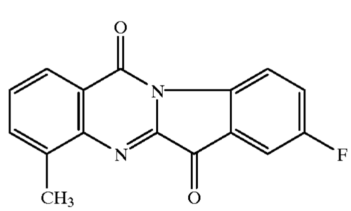 | (5.76) | (10.17) | | |

TABLE 1-continued

In Vitro Antimalarial Activity. Concentration of Indolo[2,3-b]quinazoline-6,12-dione
Inhibiting uptake of [³H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 15. | 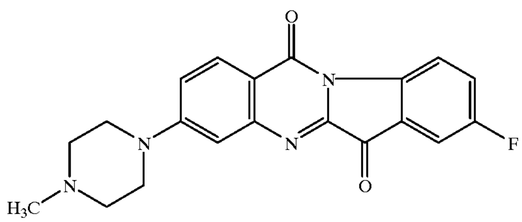 | (81.99) | (125.58) | | |
| 16. | 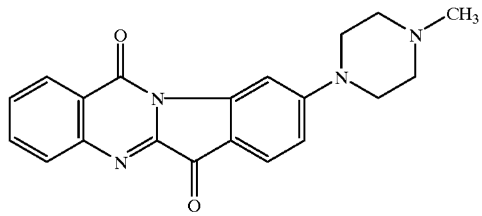 | (1014) | (2160) | | |
| 17. | 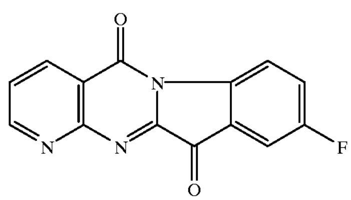 | (0.84) 2.125 | (1.53) 4.928 | 4.207 | 9.932 8.002 |
| 18. | 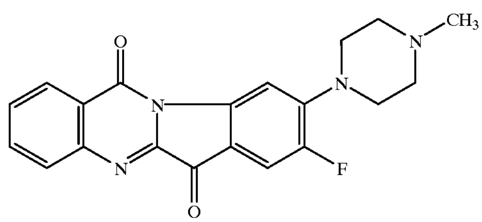 | (512.93) | (812.73) | | |
| 19. | 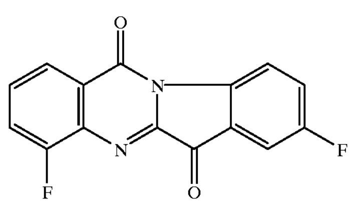 | (1.58) 8.138 | (2.57) 13.523 | 9.784 | 18.937 .485 |
| 20. | 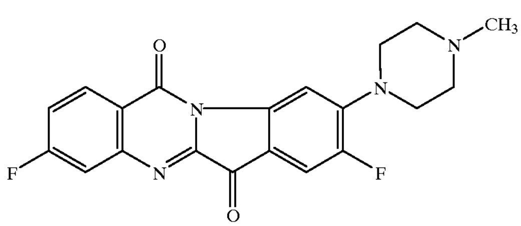 | (734.34) | (1054.46) | | |

TABLE 1-continued

In Vitro Antimalarial Activity. Concentration of Indolo[2,3-b]quinazoline-6,12-dione
Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 21. | 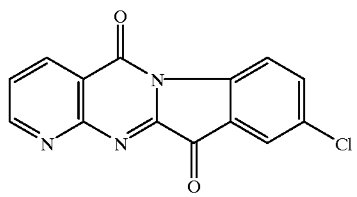 | (0.43) 1.278 | (0.93) 0.926 | 2.302 | 2.997 1.349 |
| 22. | 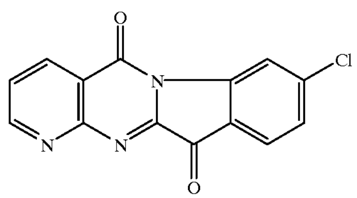 | (262.92) | (277.72) | | |
| 23. | 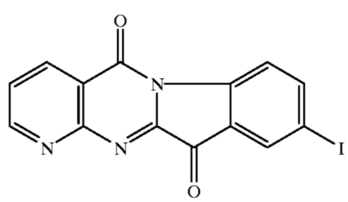 | (1.67) | (3.97) | | |
| 24. | 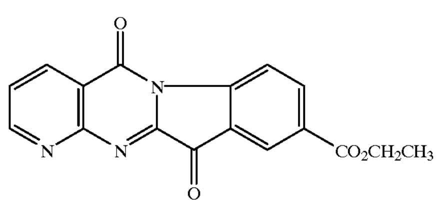 | (0.91) 0.912 4.638 | (2.01) 10.078 | 7.782 | 17.411 8.059 |
| 25. | 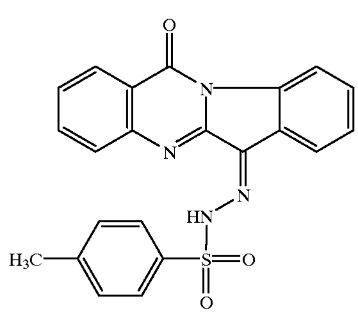 | (1990.37) | (1842.69) | | |
| 26. | 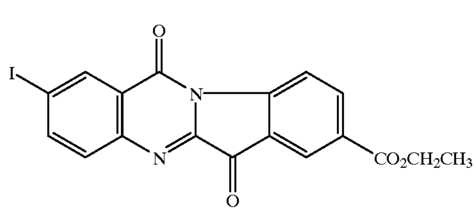 | (609.29) | (589.01) | | |

TABLE 1-continued

In Vitro Antimalarial Activity. Concentration of Indolo[2,3-b]quinazoline-6,12-dione
Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 27. | 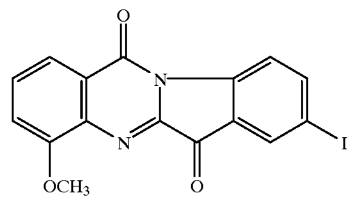 | (1.79) 35.649 | (3.01) 95.331 | 41.090 | 139.605 5.86 |
| 28. | 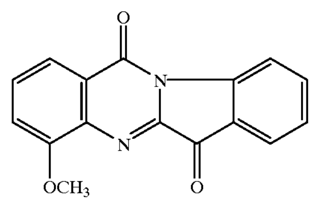 | (126) (19.925) | (124) (38.541) | | |
| 29. | 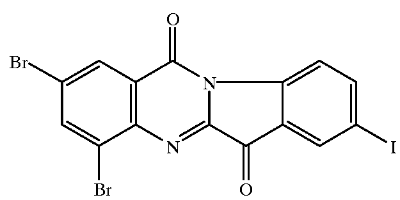 | (130.58) | (149.32) | | |
| 30. | 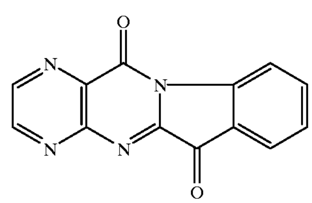 | (354.29) | (499.81) | | |
| 31. | 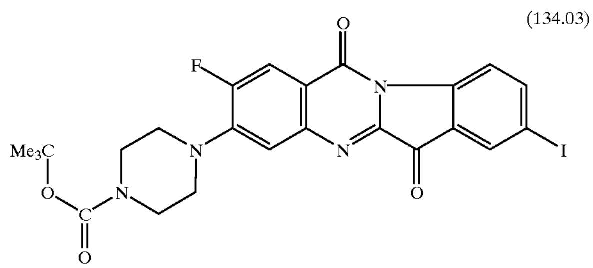 | (134.03) | (160.67) | | |
| 32. | 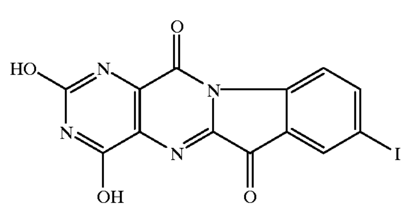 | (2588.82) | (3848.62) | | |

TABLE 1-continued

In Vitro Antimalarial Activity. Concentration of Indolo[2,3-b]quinazoline-6,12-dione
Inhibiting uptake of [³H]Hypoxanthine by Parasitized Red Blood Cells by 50% ($IC_{50}$, ng/mL)

| Example No. | Structure | $IC_{50}$ (W-2) | $IC_{50}$ (D-6) | $IC_{50}$ (TM90C2B) | $IC_{50}$ (WR75-TM9) |
|---|---|---|---|---|---|
| 33. | 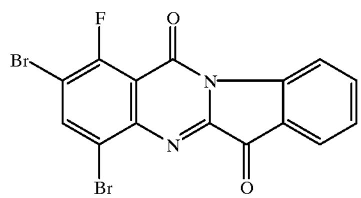 | (79.58) | (67.06) | | |
| 34. | 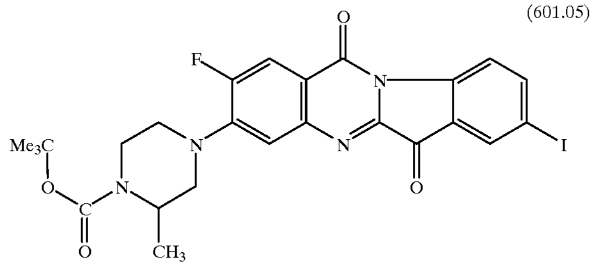 | (601.05) | (588.27) | | |
| 35. | 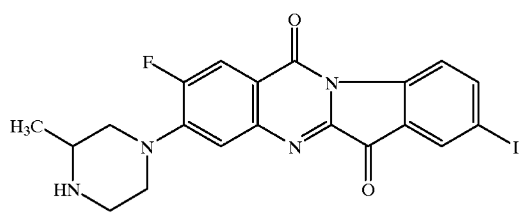 | (133.86) | (103.44) | | |
| 36. | 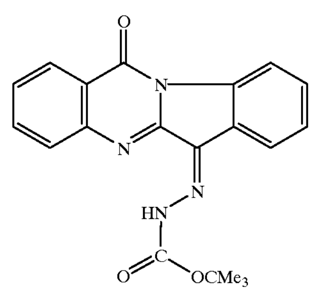 | (4815.61) | (4204.57) | | |
| 37. | 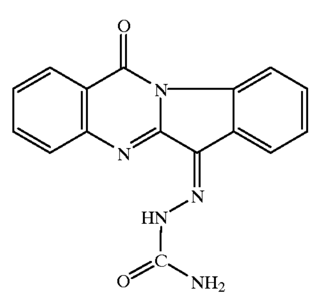 | (3483.15) | (3778.15) | | |

TABLE 1-continued

In Vitro Antimalarial Activity. Concentration of Indolo[2,3-b]quinazoline-6,12-dione Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 38. | 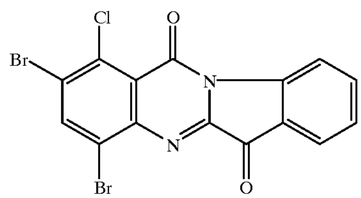 | (203.16) | (241.86) | | |
| 39. | 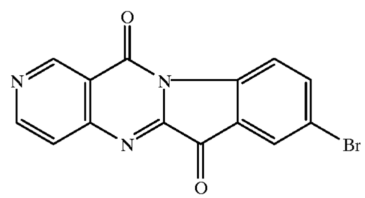 | (1.88) 1.870 | (3.57) 3.570 | 46.039 | 4.203 |
| 40. | No entry | | | | |
| 41. | 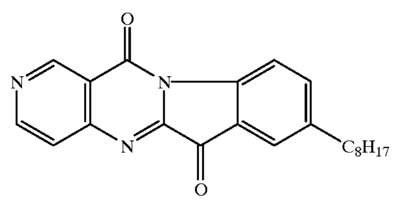 | (7.66) | (12.34) | | |
| 42. | 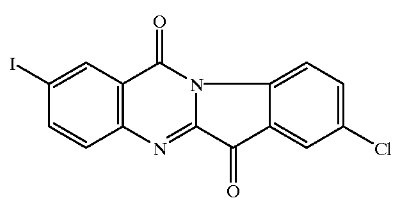 | (63.17) | (76.43) | | |
| 43. | 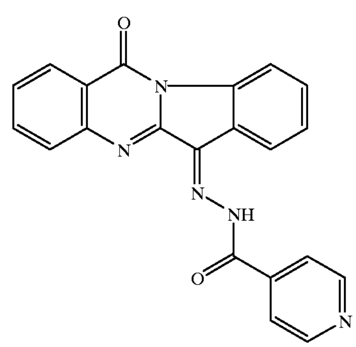 | (23,000) | (38,236) | | |
| 44. | 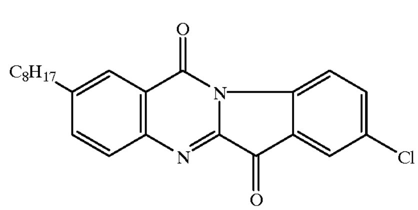 | (5859.64) | (6924.46) | | |

TABLE 1-continued

In Vitro Antimalarial Activity. Concentration of Indolo[2,3-b]quinazoline-6,12-dione
Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 45. | 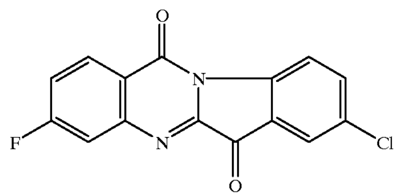 | (0.728) 4.741 | (1.28) 6.767 | 8.759 1.147 | 14.152 |
| 46. | 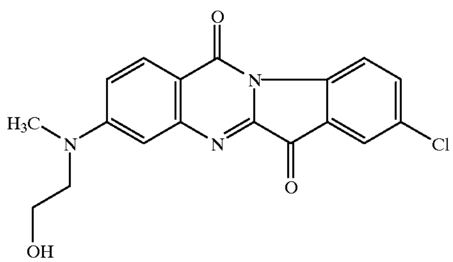 | (6.32) 22.995 | (7.61) 42.612 | 24.417 | 66.441 |
| 47. | No Entry | | | | |
| 48. | | (7.74) 58.100 | (13.9) 97.106 | 55.796 | 66.666 157.162 |
| 48. | | (508.19) | (584.37) | | |
| 49. | 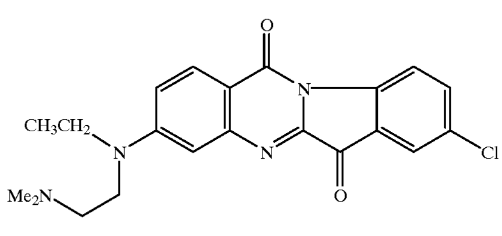 | (74.75) | (73.93) | | |
| 50. | 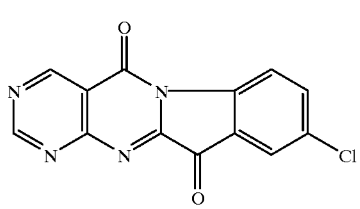 | (11.16) | (44.22) | | |

TABLE 1-continued

In Vitro Antimalarial Activity. Concentration of Indolo[2,3-b]quinazoline-6,12-dione
Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 51. | 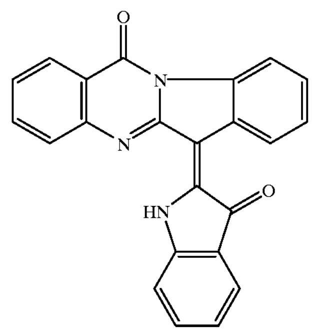 | (8760) | (8693) | | |
| 52. | 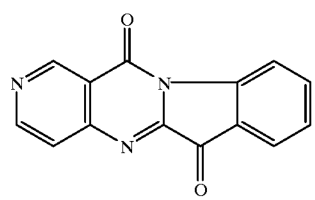 | (64.69) | (73.33) | | |
| 53. | 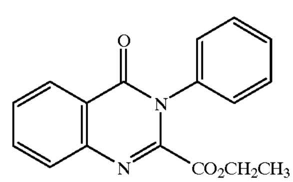 | (4872.21) | (9006) | | |
| 54. | 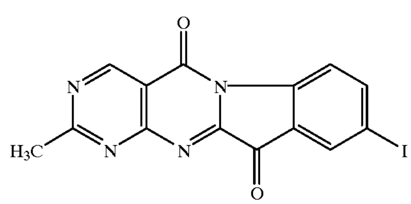 | (124.03) | (74.58) | | |
| 55. | 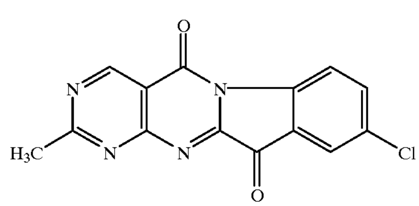 | (2.1) 2.303 | (7.2) 11.238 | 5.483 | 14.216 |
| 56. | 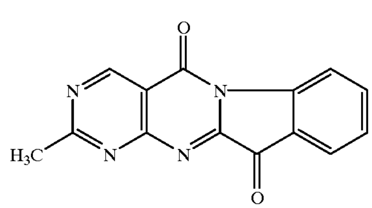 | (117) | (216) | | |

TABLE 1-continued

In Vitro Antimalarial Activity. Concentration of Indolo[2,3-b]quinazoline-6,12-dione
Inhibiting uptake of [³H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 57. | 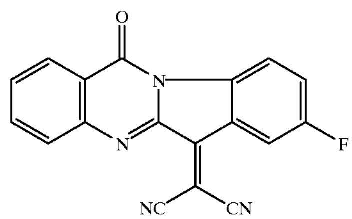 | (10.58) 28.943 | (20.33) 46.492 | 62.233 | 82.551 |
| 58. | 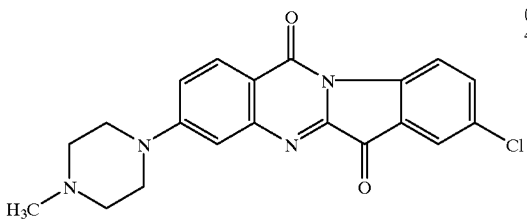 | (2.73) 4.272 | (4.52) 10.461 | 8.095 | 17.291 |
| 59. | 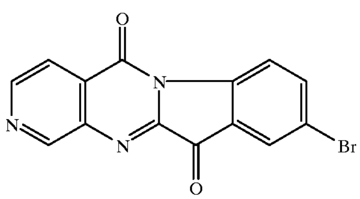 | (2.47) 17.707 | (4.37) 37.894 | 24.005 | 50.842 1.306 |
| 60. | 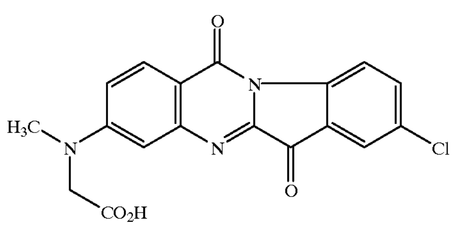 | (67.86) | (78.08) | | |
| 61. | 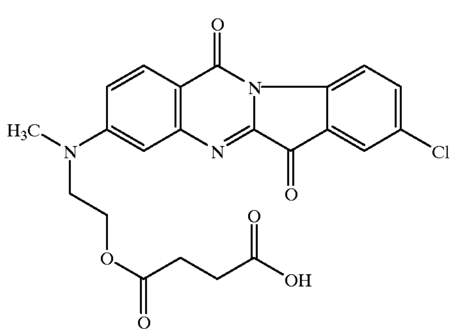 | (187) | (247) | | |
| 62. | 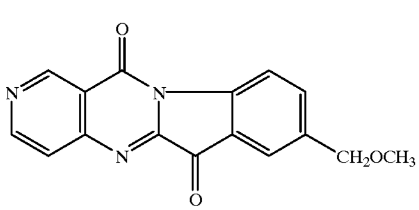 | (16) | (31.27) | | |

TABLE 1-continued

In Vitro Antimalarial Activity. Concentration of Indolo[2,3-b]quinazoline-6,12-dione
Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 63. | 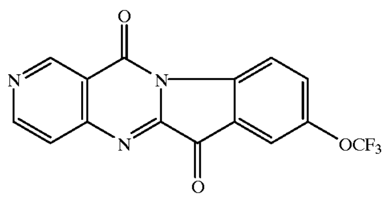 | (1.5) 1.228 | (3.16) 0.946 | 1.162 | 1.965 |
| 64. | 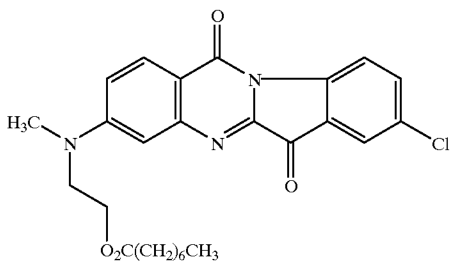 | (9.25) 36.831 | (15.86) 70.142 | 38.338 | 38.389 |
| 65. | 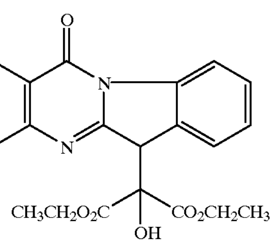 | (153.98) | (258.88) | | |
| 66. | 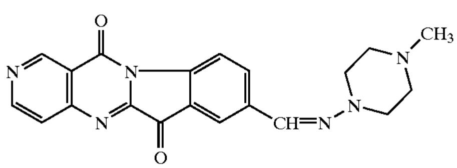 | (448.53) | (516.51) | | |
| 67. | 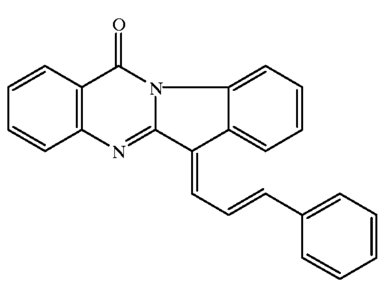 | (4423.91) | (4435.40) | | |
| 68. | 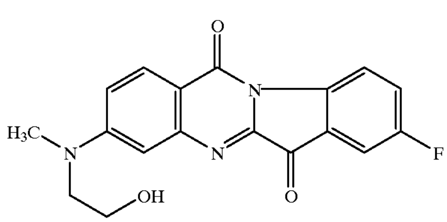 | (3.86) 2.455 | (7.86) 4.121 | 3.731 | 5.469 |

TABLE 1-continued

In Vitro Antimalarial Activity. Concentration of Indolo[2,3-b]quinazoline-6,12-dione
Inhibiting uptake of [³H]Hypoxanthine by Parasitized Red Blood Cells by 50% ($IC_{50}$, ng/mL)

| Example No. | Structure | $IC_{50}$ (W-2) | $IC_{50}$ (D-6) | $IC_{50}$ (TM90C2B) | $IC_{50}$ (WR75-TM9) |
|---|---|---|---|---|---|
| 69. | 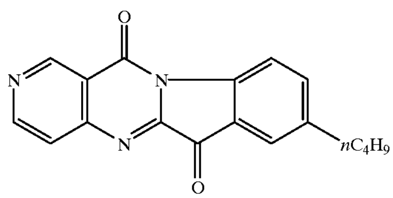 | 2.13) 8.494 | (4.04) 12.333 | 10.170 | 23.876 |
| 70. | 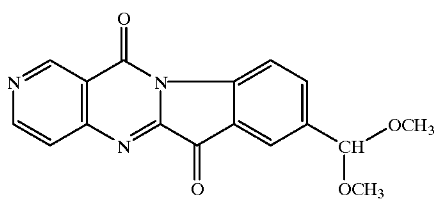 | (8.69) 6.098 | (13.22) 5.736 77.808 | 10.999 | 24.37 |
| 71. | 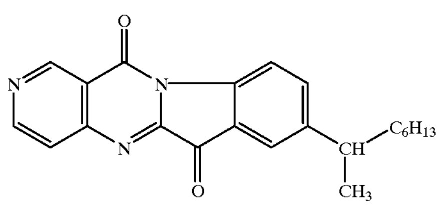 | (120.06) | (143.32) | | |
| 72. | 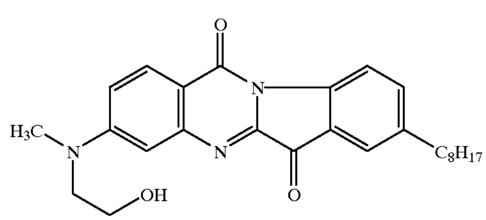 | (7465) | (7860) | | |
| 73. | 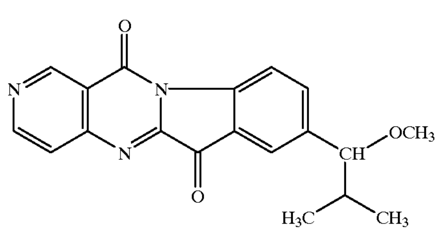 | (3.75) 2.855 | (5.40) 4.889 | 4.464 | 10.506 |
| 74. | 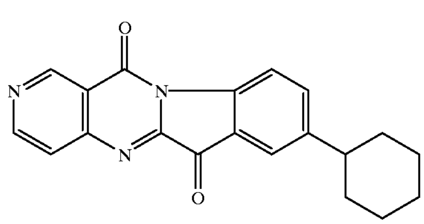 | (3.52) 59.846 | (2.19) 79.578 | 42.505 | 127.39 |

TABLE 1-continued

In Vitro Antimalarial Activity. Concentration of Indolo[2,3-b]quinazoline-6,12-dione
Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 75. | 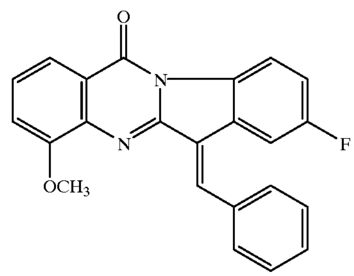 | (572.94) | (534.47) | | |
| 76. | 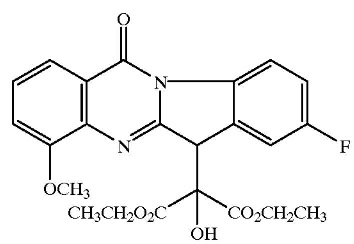 | (159.65) | (223.53) | | |
| 77. | 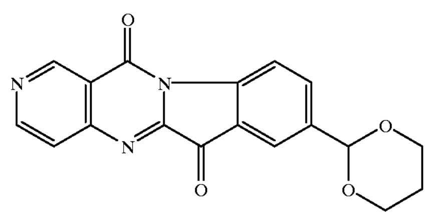 | (165.32) | (220.3) | | |
| 78. | 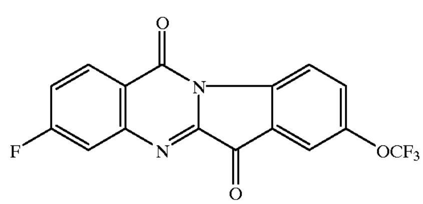 | (0.86) 0.935 | (0.93) 1.966 | 1.764 | 3.297 |
| 79. | 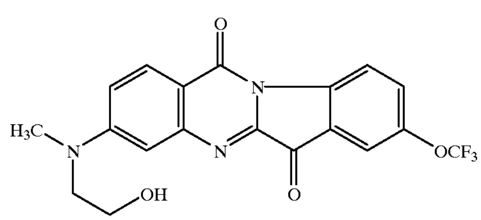 | (68.76) | (69.96) | | |
| 80. | 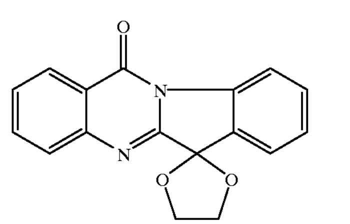 | (6902.53) | (7965.51) | | |

TABLE 1-continued

*In Vitro Antimalarial Activity. Concentration of Indolo[2,3-b]quinazoline-6,12-dione Inhibiting uptake of [³H]Hypoxanthine by Parasitized Red Blood Cells by 50% (IC$_{50}$, ng/mL)*

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 81. | 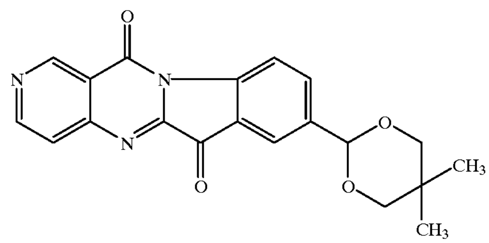 | (73.92) | (110.16) | | |
| 82. | 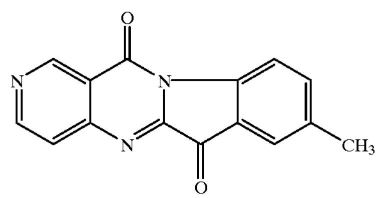 | (124) | (62.82) | | |
| 83. | 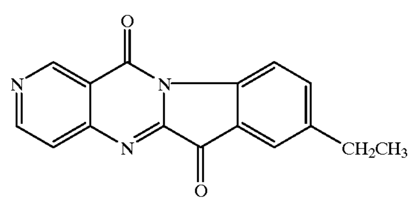 | (1.8) 7.186 | (3.11) 15.141 | 12.864 | 25.717 |
| 84. | 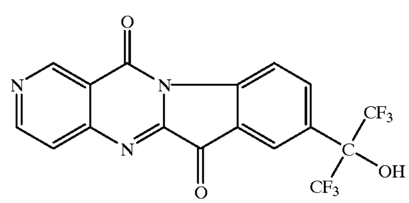 | (937.57) | (1710.33) | | |
| 85. | 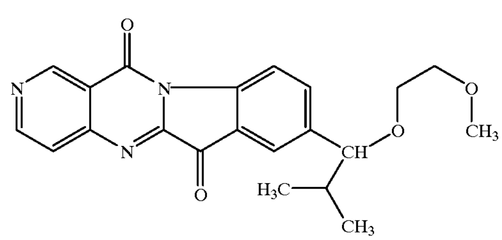 | (105.36) | (135.96) | | |
| 86. | 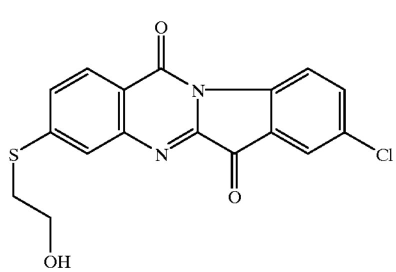 | (2.3) 1.908 | (3.6) 3.63 | 2.079 | 35.678 4.506 |

TABLE 1-continued

In Vitro Antimalarial Activity. Concentration of Indolo[2,3-b]quinazoline-6,12-dione
Inhibiting uptake of [$^3$H]Hypoxanthine by Parasitized Red Blood Cells by 50% (IC$_{50}$, ng/mL)

| Example No. | Structure | IC$_{50}$ (W-2) | IC$_{50}$ (D-6) | IC$_{50}$ (TM90C2B) | IC$_{50}$ (WR75-TM9) |
|---|---|---|---|---|---|
| 87. | 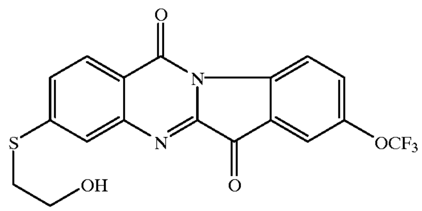 | (3.51) 1.252 | (4.92) 2.310 | 0.696 | 4.438 |
| 88. | 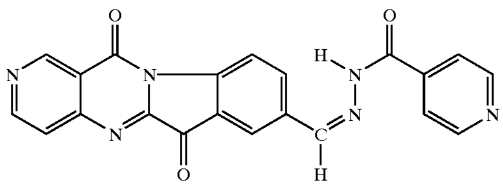 | (177.45) | (490.16) | | |
| 89. | 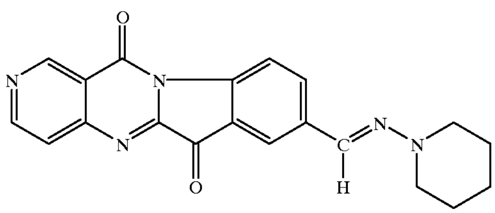 | (68.77) | (111.69) | | |
| 90. | 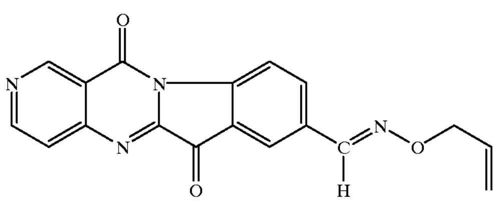 | (3.93) 15.601 | (7.59) 16.320 | 6.145 | 30.045 |
| 91. | 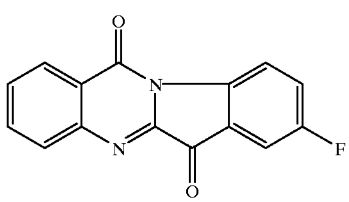 | (1.8) 5.521 4.977 | (0.24) 9.064 10.137 | 9.825 4.594 | 9.941 5.438 4.449 9.941 16.412 |

*Values in parenthesis represent assays conducted in Albumax.
**Values without parenthesis represent assays conducted in blood plasma.

Regarding the foregoing compounds, MW refers to molecular weight, W2 refers to a malaria parasite which is susceptible to mefloquine but resistant to chloroquine, sulfadoxine, pyrimethamine and quinine. D6 refers to a malaria parasite which is naturally resistant to mefloquine but susceptible to chloroquine, sulfadoxine, pyrimethamine and quinine. The numbers associated with both W2 and D6 refer to IC$_{50}$ values and the units are ng/ml.

As is shown in Table 1, the compounds 1–91 of the present are effective in treating/reducing malaria parasites. It can be seen that the lower the IC$_{50}$ concentration, the more effective the compound. The most effective compounds tested were compounds 21, 63, and 78.

The compounds of the invention are useful in the study of the treatment of malaria in vitro.

Lin, A. J.; Zikry, A. B.; Kyle, D. E. *J. Med. Chem.*, 1997, 40 (9), 1399–1400, which disclosure is herein expressly incorporated by reference, describes in detail the procedures followed by the inventors for in vitro antimalarial studies. That disclosure also describes the procedures for conducting in vivo antimalarial studies.

EXAMPLE 2

In Vivo Inhibition of *Plasmodium falciparum, Plasmodium ovale, Plasmodium malariae* and *Plasmodium vivax*

The in vivo efficacy of the compounds of the present invention alone or in combination with an adjuvant can be determined in a modified Thompson test. This test measures the survivability of mice and parasitemia clearance following administration of the compound or composition of the invention on days 3–5 post infection. In brief, $5\times10^5$ malaria parasites of one or more of the four described strains are inoculated intraperitoneally to female mice that weight approximately 24–30 g. Each compound is dissolved in 5% sodium bicarbonate, and is administered p.o. twice daily from day 3 to day 5 postinfection. Total dosage of the compounds of the invention is 0.001 to 1000 mg/kg. The percent suppression of parasitemia in the treated mice compared to untreated controls is determined for each test compound. Survival of mice to day 60 postinfection is considered a cure. Compounds are considered active when the survival time of the treated mice is greater than twice the control mice.

When the compounds of the present invention are administered with an adjuvant, the amount of adjuvant given is 0.001 to 1000 mg/kg body weight.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, bydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts of the compounds of Formula I include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of Formula I, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Other representative organic amines useful for the formation of base addition salts include diethylamine, ethylenediamine, ethanolamine, diethanolamine, piperazine and the like. The compounds of the invention are useful in vitro in inhibiting the growth of malaria parasite, and in vivo in human and animal hosts for treating malarial parasitic infections. The compounds may be used alone or in compositions together with a pharmaceutically acceptable carrier.

Total daily dose administered to a host in single or divided doses may be in amounts, for example, from 0.001 to 1000 mg/kg body weight daily and more preferred from 1.0 to 50 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium Stuart. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by monoamellar or multiamellar hydrated liquid crystals that are dispersed in an aqueous medium. Any nontoxic, physiologically acceptable and metabolizable lipid capable of forming liposomes can be used. The present compositions in liposome form can contain, in addition to the compound of the present invention, stabilizers, preservatives, excipients, and the like which are well known in the art of formulation of drugs. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W. (1976), p.33 et seq.

While the compounds of the invention can be administered as the sole active pharmaceutical agent, they can also be used in combination with one or more other agents used in the treatment of malarial parasitic infections. Representative agents useful in combination with the compounds of the invention for the treatment of malaria include, for example, quinine, mefloquine, chloroquine, halofantrine, primaquine, sulfadoxine, sulfalene, pyrimethamine, doxycycline, tetracycline, azithromycin, proguanil, cycloguanil, dapsone, artemsinin, artesunate, artemether, atovoquone and the like.

The above compounds to be employed in combination with the indolo[2,1-b]quinazoline-6,12-dione compounds of the invention will be used in therapeutic amounts as indicated in the Physicians' Desk Reference (PDR) 51st Edition (1997), which is incorporated herein by reference, or such therapeutically useful amounts as would be known to one of ordinary skill in the art such as from 0.001 to 1000 mg/kg body weight daily. The compounds of the invention and the other antiinfective agent can be administered together at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions which are given at the same time or different times, or the therapeutic agents can be given as a single composition.

While the preferred embodiments of the invention have been illustrated and described, it will be appreciated that various changes can be made therein without departing from the spirit and scope of the invention.

1. U.S. Pat. No. 5,441,955 "Indolo[2,1-b]quinazoline-6,12-dione Antibacterial Compounds and Methods of Use Thereof"
2. Mitscher, et al., "Antimicrobial Agents from Higher Plants, New Synthesis and Bioactivity of Tryptanthrin (Indolo[2,1-b]quinzoline-6,12-dione) and its Analogoues", Heterocycles 15, 1017–1021 (1981)
3. Honda, G. and Tabata., M., "Isolation of Antifungal Principal Tryptanthrin from *Strobilanthes Cusia* O. Kuntze, ", Planta Medica, J Med. Plant Res., 36, 85–86 (1979).
4. Part 1. Antitubercular Agents from Higher Plants: Synthesis and In Vitro Activity of Indolo[2,1-b]quinazoline-6,12-diones and Related Analogs, Mitscher, L, et al., Abstracts of Papers, 35 International Congress of Antimicrobial Agents and Chemotherapy, Abstract F16, San Diego, Calif., 1995.
5. Baker, W. "Part II. Antitubercular Agents from Higher Plants: Antimycobacterial Activity of Azaindoloquinazolines. Novel Agents against Sensitive and Multi-drug Resistant Tuberculosis", Abstracts of Papers, 35 International Congress of Antimicrobial Agents and Chemotherapy, Abstract F17, San Diego, Calif., 1995.
6. Bergman, J., et al., "The Structure of Some Indolic Constituents in Couroupita Guaianensis Aubl., Tetrahedron Letters, 30, 2625–2626 (1977).
7. Lin, A. J.; Zikry, A. B.; Kyle, D. E. *J. Med. Chem.,* 1997, 40 (9), 1399–1400.
11. R. E. Desjardins, C. J. Canfield, D. E. Haynes, and J. D. Chulay, Quantitative Assessment of Activity In Vitro by a Semiautomated Microdilution Technique, Antimicrob. Agents Chemother., 16, 710–718-(1979).
12. J. D. Chulay, J. D. Haynes, and C. L. Diggs, *Plasmodium falciparum*: Assessment of In Vitro Growth by [$^3$H] hypoxanthine Incorporation, Exp. Parasitol., 55, 138–146 (1983).

We claim:

1. A method of treating malaria in a host caused by malaria parasites comprising:

contacting said malaria parasites in said host with a pharmaceutically effective, growth inhibiting amount of an antimalaria compostion comprising one or more indolo[2,1-b]quinazoline-6,12-dione compounds of Formula I:

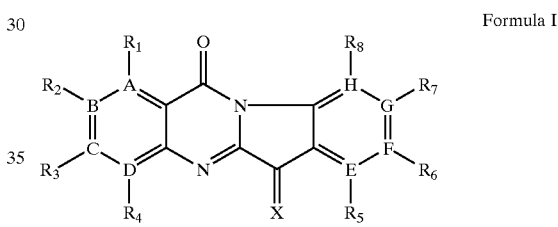

Formula I wherein A, B, C, D, E, F, G and H are independently selected from carbon and nitrogen, or A and B or C and D can be taken together to be nitrogen or sulfur, with the proviso that not more than three of A, B, C, D, E, F, G and H are other than carbon; wherein $R_1$ through $R_8$ are independently selected from the group consisting of, but not limited to F, Cl, Br, I, alkyl groups, trifluoromethyl groups, methoxyl groups, a carboxy methyl or a carboxy ethyl group ($COOCH_3$ or $COOCH_2CH_3$), nitro, aryl, heteroaryl, cyano, amino, dialkylaminoalkyl, 1-(4-alkylpiperazinyl), and pharmaceutically acceptable salts thereof; and wherein X is independently selected from the group consisting of oxygen and a side chain rendering the indolo[2,1-b]quinazoline-6,12-dione compound a prodrug; and inhibiting the growth of said malaria parasites.

2. The method of claim 1, wherein said malaria parasites are one or more of the strains of the group consisting of *Plasmodium falciparum, Plasmodium ovale, Plasmodium malariae* and *Plasmodium vivax.*

3. The method of claim 1, wherein said malaria parasites are a sensitive-strain resistant origin or a multi-drug resistant strain origin.

4. The method of claim 1, wherein said antimalarial composition further comprises an adjuvant.

5. The method of claim 1, wherein the indolo[2,1-b]quinazoline-6,12-dione compound is a prodrug.

6. The method of claim 5, where said prodrug comprises the Formula II

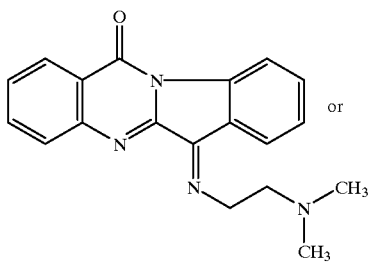

Formula II

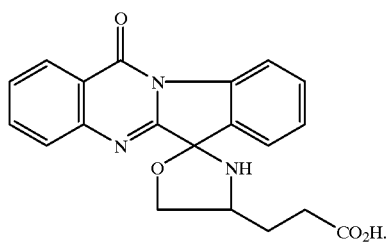

Formula III

7. The method of claim 1, further comprises contacting said malaria parasites with one or more additional antimalarial drugs selected from the group consisting of mefloquine, halofantrine, artesunate, artemether, chloroquine, halofantrine, primaquine, sulfadoxine, sulfalene, pyrimethamine, doxycycline, tetracycline, azithromycine, proguanil, cycloguanil, dapsone, artemsinin and atovoquone.

8. The method of claim 7, wherein said compound of the Formula I and said additional antimalarial drug contact said malaria parasites together in a single dosage form or separately in separate dosage forms given simultaneously or at different times.

9. The method of claim 1, wherein said composition of the Formula I is in the form of salts derived from inorganic or organic acids.

10. The method of claim 9, wherein said salts are selected from the group consisting of acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, bydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate.

11. The method of claim 1, wherein said composition is water soluble, oil-soluble or dispersible.

12. The method of claim 1, wherein said composition of the Formula I is in the form of pharmaceutically acceptable acid addition salts.

13. The method of claim 12, wherein said acid addition salts are formed with hydrochloric acid, sulphuric acid, phosphoric acid, oxalic acid, maleic acid succinic acid or citric acid.

14. The method of claim 1, wherein said host is contacted with said composition in a daily dose of 0.001 to 1000 mg/kg of body weight.

15. The method of claim 14, wherein said host is contacted with said composition in a daily dose of 1.0 to 50 mg/kg body weight.

16. The method of claim 4, wherein said host is contacted with said adjuvant in a daily dose of 0.001 to 1000 mg/kg of body weight.

17. The method of claim 1, wherein said composition is in the form of a tablet, inhalant, parenteral injection, oral liquid, transdermal preparation, suppository or spray.

18. The method of claim 1, wherein said contacting is via an administration given orally, parenterally, sublingually, rectally, topically or with an inhalation spray.

* * * * *